United States Patent [19]
Schwartz et al.

[11] Patent Number: 6,117,102
[45] Date of Patent: Sep. 12, 2000

[54] APPARATUS FOR FLUSHING A VASCULAR CATHETER

[75] Inventors: Robert S. Schwartz; David R. Holmes; David Berry, all of Rochester, Minn.; Donald G. Ellis, Boulder, Colo.

[73] Assignee: Mayo Foundation for Medical Education and Research, Rochester, Minn.

[21] Appl. No.: 09/159,007

[22] Filed: Sep. 23, 1998

[51] Int. Cl.[7] .................................................. A61M 1/00
[52] U.S. Cl. ................................ 604/30; 604/33; 604/246
[58] Field of Search .................................. 604/30, 33, 27, 604/246, 249, 236

[56] References Cited

U.S. PATENT DOCUMENTS

| | | | |
|---|---|---|---|
| 4,341,224 | 7/1982 | Stevens | 604/30 X |
| 4,668,215 | 5/1987 | Allgood | 604/30 |
| 5,100,377 | 3/1992 | Freitas et al. | 604/30 |
| 5,356,375 | 10/1994 | Higley. | |

*Primary Examiner*—John D. Yasko
*Attorney, Agent, or Firm*—Merchant & Gould P.C.

[57] ABSTRACT

An apparatus for flushing a vascular catheter. Inlet and outlet passages extending from inlet and outlet ports, respectively, are selectably in communication with one another via a manually operable member cooperating with a sealing member and biased toward a closed position. Mechanisms for continuously and periodically flushing the catheter are incorporated.

18 Claims, 1 Drawing Sheet

APPARATUS FOR FLUSHING A VASCULAR CATHETER

FIELD OF THE INVENTION

This invention relates generally to devices used in vascular catheter procedures, and more particularly to devices for flushing a catheter during such procedures.

BACKGROUND OF THE INVENTION

When performing diagnostic, therapeutic or interventional vascular procedures involving a catheter, it is necessary to flush the catheter (typically with saline) in order to prevent blood clots from forming. The device most commonly used today is a manifold with a number of manually operated stopcock valves. Periodically the physician or technician must manually open or close one or more stopcocks for a period of time so that saline from a high pressure source can flush the catheter. After a satisfactory amount of flushing has been done, the stopcocks are again manually moved back to their original position, and the surgeon then resumes performing the procedure.

There are a number of shortcomings with the existing manifold. One is that the physician is "hands off" from performing the procedure for a long period of time (20 seconds or more per flush), which time could instead be used to perform the procedure on the patient. Having to manually flush also breaks the continuity of the procedure, which can be distracting. It also requires that the operator (if not the physician) is at all times sterile. Another shortcoming is that flushing must be done fairly often. During each flush, blood pressure readings are interrupted, which is undesirable. Each additional flush is also another interruption, potential distraction and further delay of the procedure.

What has been needed is an apparatus for flushing a vascular catheter which automatically closes and which provides a relatively slow continuous flush of the catheter.

SUMMARY OF THE INVENTION

According to the present invention, an apparatus for flushing a vascular catheter is provided. The inventions can be used in a variety of diagnostic, therapeutic and interventional procedures involving a vascular catheter.

In one aspect of the invention, the apparatus comprises a housing having an inlet port for connection to a flushing liquid source, and an outlet port for communication with the vascular catheter. Inlet and outlet passages are in communication with the inlet and outlet ports, respectively, and are also selectively in communication with one another. A manually operable member is biased toward a closed position and moveable to an open position. A sealing member cooperates with the manually operable member such that, in the closed position, the inlet and outlet passages are sealed from one another by the sealing member; in the open position, the inlet and outlet passages are in communication with one another. Thus, when the manually operable member is released, it automatically returns to a closed position. In a preferred version, the sealing member is slowed toward a sealed position, thereby flushing the catheter for a period of time after the manually operable member has been moved to the open position.

In another aspect of the invention, the apparatus comprises a housing having an inlet port for connection to a flushing liquid source and an outlet port for communication with the vascular catheter. Mechanisms for continuously and periodically flushing are provided. The continuously flushing mechanism provides a relatively slow rate of flow of flushing fluid from the inlet port to the outlet port. The periodically flushing mechanism bypasses the continuously flushing mechanism to provide a relatively high rate of flow of flushing liquid from the inlet port to the outlet port.

These and other advantages and features of novelty which characterize the invention are pointed out with particularity in the claims annexed hereto. However, for a better understanding of the invention and its advantages, reference should be made to the drawing which forms a further part hereof, and to the accompanying descriptive matter in which there is illustrated and described a preferred embodiment of the invention.

DETAILED DESCRIPTION OF THE PREFERRED EMBODIMENT

Figure 1:
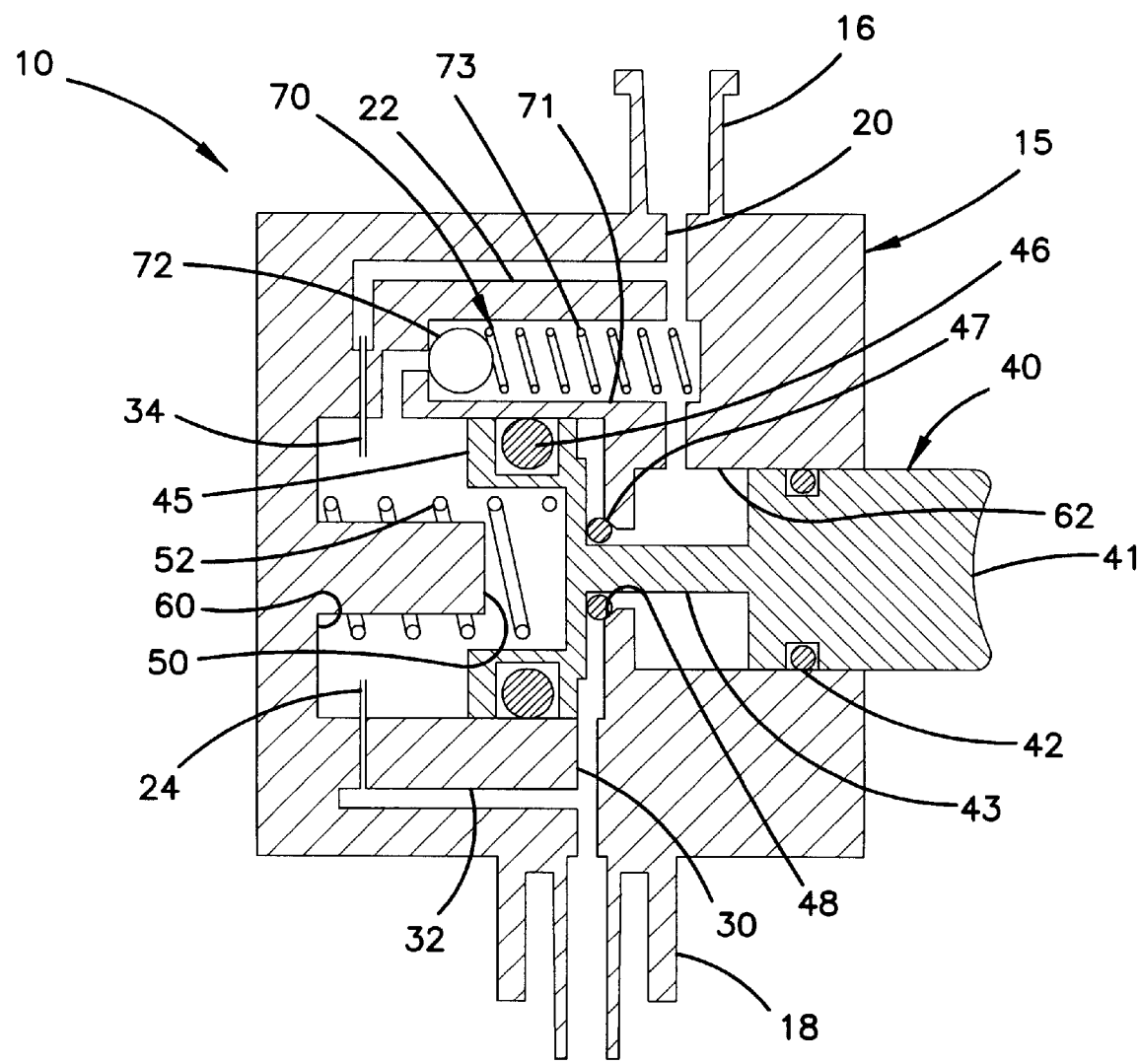
FIG. 1 is a cross-sectional view of an apparatus for flushing a vascular catheter according to the present invention.

Referring now to the drawing, an embodiment of the apparatus of the present invention for flushing a vascular catheter is shown in FIG. 1.

Apparatus 10 comprises housing 15 including inlet 16 and outlet 18 ports. Inlet port 16 is for connection to a high pressure liquid (typically saline) flushing source as is commonly used. Outlet port 18 is for communication with the vascular catheter, typically through a hemostasis valve.

Apparatus 10 is constructed so that it will automatically return to a closed position after its manually operable member 40 is moved to an open position. Member 40 includes button 41, stem 43, and sealing member 45 configured as a piston, the latter two constituting a plunger. Inlet 20 and outlet 30 passages provide communication between inlet 16 and outlet 18 ports, respectively, and bypass chamber 62. O-rings 42, 47 on button 41 and stem 43 seal chamber 62. When button 41 is depressed, O-ring 47 moves away from seating surface 48, thereby causing flushing liquid to pass from inlet passage 20, through bypass chamber 62 and out outlet port 18 to the catheter. Manually operable member 40 and sealing member 45 are biased toward a closed position (shown) by compression spring 52 on plunger stop 50. Plunger stop 50 defines the end of the open position by sealing member 45 abutting against it.

It will be understood that this arrangement could be varied in a number of ways within the principles of the invention. For example, a lever could be employed instead of a button and plunger. The manually operable member and sealing member also need not be an integral part. A variety of springs (or spring means) could also be employed, and the spring could act on either the operable member or the sealing member.

Apparatus 10 also provides a mechanism by which sealing member 45 is slowed to a closed position so that high pressure flushing fluid continues to flush the catheter after operable member 40 is released. This is accomplished by capillaries 24, 34 and timing chamber 60. Chamber 60 is sealed by O-ring 46 on sealing member 45. When sealing member 45 begins to move out of chamber 60 (to the right in figure), low pressure on the bottom (left in figure) side of sealing member 45 keeps manually operable members 40 from moving back to an extended position. Member 40 gradually moves to the extended position as saline is drawn into timing chamber 60 through capillaries 24, 34, which receive flushing liquid from inlet 20 and outlet 30 passages via capillary inlet 22 and outlet 32 passages. As flushing liquid from capillaries 24, 34 slowly fills timing chamber 60, after a period of time sealing and operable member 40 returns to the extended position, and O-ring 47 closes bypass chamber 62, thereby ending the bypass of high rate liquid flush.

The preferred amount of bypass time is preferably about 20 seconds. The design parameters of the various parts involved could be varied to achieve this. In the preferred version, sealing member 45 has a stroke length of 0.29 inches and a diameter of 0.75 inches. Capillaries 24, 34 are 0.30 inches long and have an inside diameter of 0.0060 inches, resulting in a conductance of approximately 0.04 cubic inches/minute/psi. The mean effective force of spring 52 is about 4 pounds.

It will be understood that a variety of other mechanisms could be employed to slow the movement of the sealing member to the closed position. For example, air from the atmosphere could be drawn through a pin hole into a timing chamber to provide the necessary resistance. Other approaches using air, liquid, another spring means or other mechanisms could also be employed.

Check valve 70 is provided to expel liquid from timing chamber 60 when button 41 is depressed. Check valve 70 includes spring 73 biasing ball 72 to a closed position (shown). When button 41 is depressed, capillaries 24, 34 resist flow through them so that ball 72 unseats and liquid flows from timing chamber 60, through passage 71 and out inlet port 16. A variety of other arrangements could be employed to similarly expel liquid or air from a timing chamber.

Apparatus also provides a relatively slow rate continuous flush of the catheter. This is accomplished by capillaries 24, 34 creating a slow flow from inlet port 16 to outlet port 18 via timing chamber 60. The rate of flow is a slow drip, on the order of 1.0 ml./min. (at 300 mm. Hg pressure drop), resulting in a conductance of 0.010 cubic inches/minute/psi from the above capillary specifications.

In this way, capillaries 24, 34 serve dual roles. They provide for a slow rate continuous flush, and they also act as the resistance mechanism for slowing the movement of operable member 40 to a bypass closed position.

It will be understood that the apparatus could be modified in a number of ways to provide both continuous flushing and periodic flushing that bypasses the continuous flushing mechanism. A variety of mechanical and electronic means, or a combination thereof, could be employed to achieve this end. Periodic flushing could also be done automatically instead of manually.

It should be understood that the present invention is not limited to the preferred embodiment discussed above, which is illustrative only. Changes may be made in detail, especially in matters of the type, arrangement, shape and size of components within the principles of the invention, to the full extent indicated by the broad general meanings of the terms in which the appended claims are expressed.

We claim:

1. An apparatus for flushing a vascular catheter, comprising:
    (a) a housing having an inlet port for connection to a flushing liquid source and an outlet port for communication with the vascular catheter;
    (b) inlet and outlet passages in communication with said inlet and outlet ports, respectively, and selectably in communication with one another;
    (c) a manually operable member biased toward a closed position and movable to an open position; and
    (d) a sealing member cooperating with said manually operable member, wherein in said closed position said inlet and outlet passages are sealed from one another by said sealing member, and in said open position said inlet and outlet passages are in communication with one another;
    (e) said sealing member constructed and arranged such that a movement of said sealing member toward a sealed position is substantially slowed, thereby flushing the vascular catheter for a period of time after said manually operable member has been moved to said open position.

2. An apparatus for flushing a vascular catheter according to claim 1, wherein said manually operable member is a button movable between extended and depressed positions corresponding to said closed and open positions respectively.

3. An apparatus for flushing a vascular catheter according to claim 2, wherein said sealing member is a plunger having a sealing gasket around it, said plunger being rigidly connected to said button.

4. An apparatus for flushing a vascular catheter according to claim 1, wherein said manually operable member is biased toward said closed position by a spring.

5. An apparatus for flushing a vascular catheter according to claim 1, wherein said movement of said sealing member toward said sealed position is slowed by means for creating a temporary differential pressure pulling said sealing member away from said sealed position.

6. An apparatus for flushing a vascular catheter according to claim 5, wherein said pressure differential creating means comprise a sealed chamber having an inlet into which fluid slowly flows.

7. An apparatus for flushing a vascular catheter according to claim 6, wherein said apparatus is constructed and arranged such that said fluid is flushing liquid received from said inlet port.

8. An apparatus for flushing a vascular catheter according to claim 6, further including means for expelling fluid from said chamber when said sealing member is moved into said chamber.

9. An apparatus for flushing a vascular catheter according to claim 1, further including means for continuously flushing the vascular catheter by providing a relatively slow rate of flow of flushing liquid from said inlet port to said outlet port.

10. An apparatus for flushing a vascular catheter according to claim 9, wherein said continuously flushing means are also employed to slow a movement of said sealing member to a sealed position.

11. An apparatus for flushing a vascular catheter, comprising:
    (a) a housing having an inlet port for connection to a flushing liquid source and an outlet port for communication with the vascular catheter;
    (b) means for continuously flushing the vascular catheter by providing a relatively slow rate of flow of flushing liquid from said inlet port to said outlet port;
    (c) means for periodically flushing the vascular catheter by bypassing said continuously flushing means to provide a relatively high rate of flow of flushing liquid from said inlet port to said outlet port; and
    (d) said periodic flushing means including a manually operable member constructed and arranged such that, after being moved to a bypass position, a movement of said member toward a closed position is substantially slowed, thereby continuing to flush the vascular catheter at a relatively high rate for a period of time after said manually operable member has been moved to said bypass position.

12. An apparatus for flushing a vascular catheter according to claim 11, wherein said continuous flushing means comprise a capillary tube providing flushing fluid at a rate of about between 0.10 and 10.0 cubic centimeters per minute.

13. An apparatus for flushing a vascular catheter according to claim 11, wherein said manually operable member is a button biased toward said closed position by a compression spring.

14. An apparatus for flushing a vascular catheter according to claim 11, wherein said movement of said manually operable member toward said closed position is slowed by means for creating a temporary pressure differential pulling said manually operable member away from said closed position.

15. An apparatus for flushing a vascular catheter according to claim 14, wherein said pressure differential creating means comprise a sealed chamber having an inlet into which fluid slowly flows.

16. An apparatus for flushing a vascular catheter according to claim 15, wherein said pressure differential creating means comprise at least a portion of said continuously flushing means.

17. An apparatus for flushing a vascular catheter according to claim 11, wherein said apparatus is constructed and arranged such that said period of time is at least 5 seconds.

18. An apparatus for flushing a vascular catheter according to claim 1, wherein said apparatus is constructed and arranged such that said period of time is at least 5 seconds.

* * * * *